United States Patent
Lee

(10) Patent No.: US 11,834,172 B2
(45) Date of Patent: Dec. 5, 2023

(54) METHOD OF STERILIZING VEHICLE INTERIOR USING DRONE

(71) Applicants: HYUNDAI MOTOR COMPANY, Seoul (KR); KIA MOTORS CORPORATION, Seoul (KR)

(72) Inventor: Jae Seung Lee, Hwaseong-si (KR)

(73) Assignees: HYUNDAI MOTOR COMPANY, Seoul (KR); KIA MOTORS CORPORATION, Seoul (KR)

( * ) Notice: Subject to any disclaimer, the term of this patent is extended or adjusted under 35 U.S.C. 154(b) by 298 days.

(21) Appl. No.: 17/101,887

(22) Filed: Nov. 23, 2020

(65) Prior Publication Data

US 2022/0024579 A1 Jan. 27, 2022

(30) Foreign Application Priority Data

Jul. 24, 2020 (KR) .................. 10-2020-0091992

(51) Int. Cl.
| | |
|---|---|
| B64C 39/02 | (2023.01) |
| B64D 47/00 | (2006.01) |
| A61L 2/10 | (2006.01) |
| A61L 2/24 | (2006.01) |
| A61L 9/20 | (2006.01) |

(Continued)

(52) U.S. Cl.
CPC .......... *B64C 39/024* (2013.01); *A61L 2/10* (2013.01); *A61L 2/24* (2013.01); *A61L 9/20* (2013.01); *B64D 47/00* (2013.01); *A61L 2202/14* (2013.01); *A61L 2209/111* (2013.01); *B64U 10/13* (2023.01); *B64U 30/20* (2023.01); *B64U 2101/00* (2023.01); *B64U 2201/20* (2023.01)

(58) Field of Classification Search
CPC ..... A61L 2/10; A61L 2/24; A61L 9/20; A61L 2202/14; A61L 2202/16; A61L 2202/25; A61L 2209/14; A61L 2209/111; B64C 39/024; B64C 2201/12; B64C 2201/146; B64C 2201/027; B64C 2201/108; B64D 1/18; B64D 47/00
See application file for complete search history.

(56) References Cited

U.S. PATENT DOCUMENTS

| | | | |
|---|---|---|---|
| 2012/0282135 A1 | 11/2012 | Trapani | |
| 2015/0209457 A1* | 7/2015 | Bonutti | .................. C02F 1/325 |
| | | | 250/435 |

(Continued)

FOREIGN PATENT DOCUMENTS

| | | |
|---|---|---|
| CN | 108970252 A | 12/2018 |
| CN | 110844057 A | 2/2020 |

(Continued)

*Primary Examiner* — Kevin Joyner
*Assistant Examiner* — Brady C Pilsbury
(74) *Attorney, Agent, or Firm* — LEMPIA SUMMERFIELD KATZ LLC

(57) ABSTRACT

A method of sterilizing a vehicle interior using a drone includes: receiving information on whether a passenger is boarding or the passenger has initiated a sterilization request; and when the passenger does not ride in a vehicle or the sterilization request is received from the passenger, performing, with a drone, a set of instructions to implement a sterilization logic. In particular, the sterilization logic includes determining an infected area using a sensor part, and allowing the drone to fly and performing intensive sterilization in the infected area.

7 Claims, 4 Drawing Sheets

(51) Int. Cl.
  *B64U 10/13* (2023.01)
  *B64U 30/20* (2023.01)
  *B64U 101/00* (2023.01)

(56) References Cited

U.S. PATENT DOCUMENTS

| | | |
|---|---|---|
| 2015/0290348 A1 | 10/2015 | Taoka et al. |
| 2016/0304201 A1* | 10/2016 | Kozloski .................. G01N 1/02 |
| 2018/0043782 A1* | 2/2018 | Ng ......................... B64C 39/024 |
| 2018/0118337 A1* | 5/2018 | Viel ......................... B08B 1/002 |
| 2018/0155026 A1 | 6/2018 | Policicchio et al. |
| 2018/0186212 A1* | 7/2018 | Kundu .................... A61L 9/015 |
| 2019/0117812 A1* | 4/2019 | Olsen ........................ A61L 2/26 |
| 2019/0216958 A1 | 7/2019 | Kreitenberg et al. |
| 2020/0061223 A1 | 2/2020 | Hallack |
| 2021/0299311 A1* | 9/2021 | Yu .......................... B08B 7/0057 |
| 2022/0017220 A1* | 1/2022 | Bae ......................... A47L 9/122 |
| 2022/0088250 A1* | 3/2022 | Baarman .................. A61L 2/24 |

FOREIGN PATENT DOCUMENTS

| | | | |
|---|---|---|---|
| CN | 111214680 A | 6/2020 | |
| EP | 3354291 A1 | 8/2018 | |
| KR | 101559898 B1 * | 10/2015 | |
| KR | 10-1860938 B | 5/2018 | |
| WO | WO-2020146138 A1 * | 7/2020 | ............... A61L 2/10 |

\* cited by examiner

METHOD OF STERILIZING VEHICLE INTERIOR USING DRONE

CROSS-REFERENCE TO RELATED APPLICATION

This application claims priority to and the benefit of Korean Patent Application No. 10-2020-0091992, filed on Jul. 24, 2020, the entire contents of which are incorporated herein by reference.

FIELD

The present disclosure relates to a method of sterilizing a vehicle interior using a drone. More particularly, it relates to a method of sterilizing a vehicle interior using a drone, which provides a method of determining an infected area and sterilizing a vehicle interior by allowing a drone to fly in the infected area.

BACKGROUND

The statements in this section merely provide background information related to the present disclosure and may not constitute prior art.

Generally, drones are flying objects operated by wireless control of users and are initially developed and used for military purposes. Recently, the scope of use of the drones has expanded for transportation, leisure, and industrial purposes.

Thus, in order to solve an inefficiency cleanup operation, such as application of pesticides and fertilizers, performed in a large area with insufficient hands for a long time in the primary industries such as agriculture, fisheries, and livestock, there is tendency to use the drones. The cleanup operation using the drones is getting attention as the most realistic and efficient system for solving the shortage of manpower and cost problems in the primary industries.

In addition, even in the technical field of performing sterilization so as to prevent infectious diseases in addition to the cleanup operation, there is a tendency of using the drones and technological development of using the drones is currently being conducted for various purposes.

Recently, technologies for improving driving environments of vehicles using drones which are disposed in the vehicles have been developed, and technologies for performing unmanned flight of the drones have been developed.

However, we have discovered that since the drones are located outside the vehicles and are used as targets for receiving information related to the driving of the vehicles, there is no configuration of drones which are operated in interiors of the vehicles. In addition, more customers desire to sterilize and disinfect the vehicles using drones disposed in the interiors of the vehicles, and continuous management is desired for an infected area with which a user is constant contact.

SUMMARY

In one aspect, the present disclosure provides a method of sterilizing a vehicle interior using a drone, which determines a pollution degree and size of an infected area to perform intensive sterilization.

In another aspect, the present disclosure provides a method of sterilizing a vehicle interior using a drone, which drives a purification unit when air quality is less than or equal to a reference value stored in a controller.

Objectives of the present disclosure are not limited to the above-described objectives, and other objectives of the present disclosure, which are not mentioned, can be understood by the following description and also will be apparently understood through forms of the present disclosure. Further, the objectives of the present disclosure can be implemented by means described in the appended claims and a combination thereof.

A method of sterilizing a vehicle interior using a drone for achieving the above objective of the present disclosure includes the following configurations.

In an exemplary form of the present disclosure, a method of sterilizing a vehicle interior using a drone includes: receiving information on whether a passenger is boarding or the passenger has initiated a sterilization request; and when the passenger is not present in a vehicle interior or the sterilization request is received from the passenger, performing, with a drone, a set of instructions to implement a sterilization logic. In particular, the sterilization logic includes: determining an infected area using a sensor part, and allowing the drone to fly and performing intensive sterilization in the infected area.

In addition, when a pollution degree of the infected area is greater than or equal to a first reference value, the performing of the intensive sterilization may include performing ultraviolet (UV) sterilization or disinfectant application.

In addition, when an infected zone of the infected area is greater than a reference area which is set by a controller, the performing of the UV sterilization or the disinfectant application may include applying disinfectant.

In addition, when the infected zone of the infected area is smaller than the reference area which is set by the controller, the performing of the UV sterilization or the disinfectant application may further include performing the UV sterilization.

In addition, when air quality of the infected area is less than or equal to a second reference value, the performing of the intensive sterilization may further include performing driving of a propeller of the drone and performing air purification through a purification unit.

In addition, the determining of the infected area using the sensor part may include determining a movement of a user using a terrain sensor located in the drone, and determining an area in which the movement of the user is greater than or equal to a reference movement stored in the controller as the infected area.

In addition, the determining of the movement of the user using the terrain sensor located in the drone may include: determining whether a switch input of the user is received by a vehicle controller; and when the determined area where the movement of the user is equal to or greater than the reference movement coincides with an area from which the switch input of the user is received, determining the determined area as the infected area.

In addition, the allowing of the drone to fly and the performing of the intensive sterilization in the infected area may include learning and storing a terrain of the vehicle interior using a terrain sensor located in the drone, and receiving real-time terrain information according to a flight of the drone and setting a flight path.

In addition, when the passenger is present, the allowing of the drone to fly and the performing of the intensive sterilization in the infected area may include compensating for a range of the UV sterilization and the disinfectant application.

In addition, after the allowing of the drone to fly and the performing of the intensive sterilization in the infected area are completed, the method may further include directing the drone to be docked in a vehicle in a standby state.

Other aspects and exemplary forms of the present disclosure are discussed infra.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The above and other features of the present disclosure are discussed infra.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
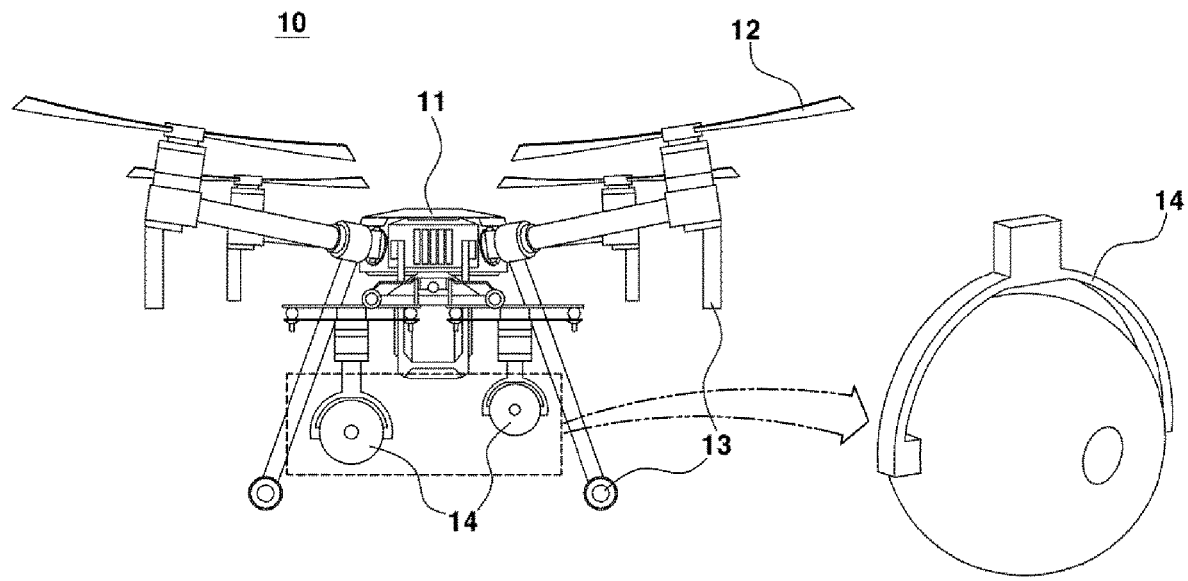
FIG. 1 is a configurational diagram illustrating a drone including an ultra violet (UV) light-emitting diode (LED) according to one form of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Hereinafter, forms of the present disclosure will be described in detail with reference to the accompanying drawings. The forms of the present disclosure can be modified in various forms, and the scope of the present disclosure should not be construed as being limited to the following forms. These forms are provided to more fully describe the present disclosure to those skilled in the art.

Further, the term "~part," "~unit," or the like used herein means a unit for processing at least one function or operation, and this unit may be implemented by hardware, software, or a combination of hardware and software.

Further, the term "infected zone" may mean part or all of the "infected area".

In addition, a term "~sensor," or the like used herein may be understood as a sub-concept of a sensor part disclosed in the claims.

It should be understood that the appended drawings are not necessarily to scale, presenting a somewhat simplified representation of various features illustrative of the basic principles of the present disclosure. The specific design features of the present disclosure as disclosed herein, including, for example, specific dimensions, orientations, locations, and shapes will be determined in part by the particular intended application and use environment.

Hereinafter, in describing with reference to the accompanying drawings, the same or corresponding components are assigned the same reference numerals, and duplicate descriptions thereof will be omitted therein.

The present disclosure relates to a method of sterilizing a vehicle interior using a drone 10, and more particularly, to flight control of the drone 10 which determines an infected area based on mutual communication between a vehicle controller located in a vehicle and a controller located in the drone 10 and performs intensive sterilization on the infected area.

The drone 10 may be located in a state of being docked on an overhead console of a vehicle and may be configured to charge a battery of the drone 10 by receiving electric power from the vehicle. In addition, when flight of the drone 10 is completed, the drone 10 is controlled to return to a docking position. In one form, the drone 10 may be located anywhere in the vehicle interior, and it is configured such that the vehicle and drone 10 are connected in a wireless manner or a wired manner and thus electric power is applied to the drone 10.

In addition, since the drone 10 may be provided from the outside of the vehicle, when the drone 10 is provided from the outside of the vehicle, the vehicle controller is configured to open a window or sunroof so as to allow the drone 10 to fly into the vehicle interior. In addition, when intensive sterilization of the vehicle is performed through the drone 10 provided from the outside, the drone 10 in which a set of instructions to implement the sterilization logic is performed is configured to fly to the outside of the vehicle using the above same method.

Figure 2:
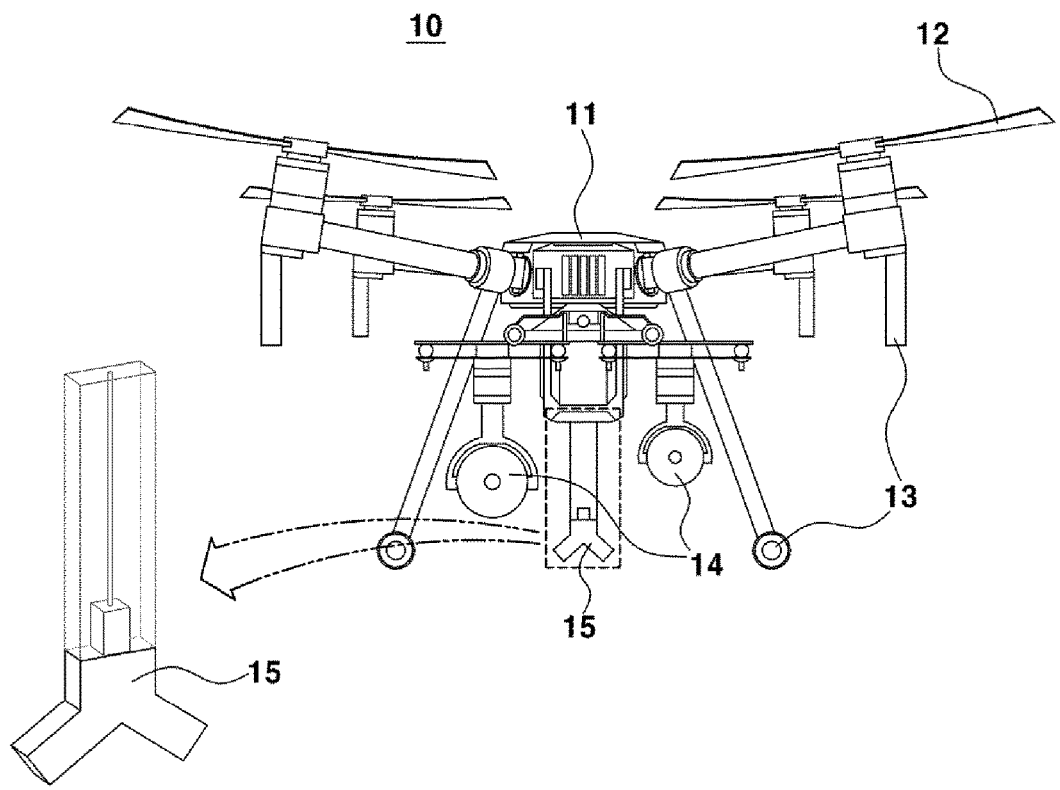
FIG. 2 is a configurational diagram illustrating the drone including a disinfectant application part according to one form of the present disclosure.
Figure 3:
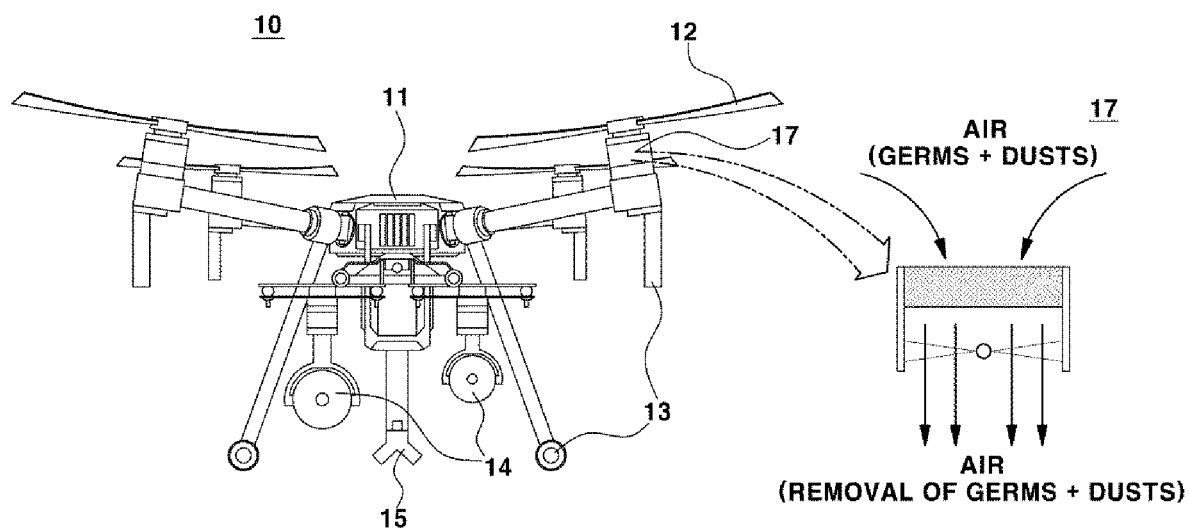
FIG. 3 is a configurational diagram illustrating the drone including a purification unit according to one form of the present disclosure.

FIGS. 1 to 3 illustrate configurational diagrams of the drone 10 and include a coupling relationship between configurations for determining an infected area and performing intensive sterilization.

The drone 10 may be located in the vehicle interior and may include a drone body 11, a drone propeller 12, terrain sensors 13 installed at a lower end of the drone body 11 and on a side surface adjacent to the drone propeller 12, a communication part for transmitting and receiving data to and from the vehicle controller, a disinfectant vessel installed in the drone body 11, an applying part 15 configured to apply disinfectant from the disinfectant vessel, and a controller configured to store data received by the terrain sensors 13 and set a flight path of the drone 10 on the basis of the stored data.

The terrain sensors 13 may include at least one light detection and ranging (LiDAR) located at the lower end of the drone 10 and one or more ultrasonic sensors located on the side surface of the drone 10.

The controller located in the drone 10 is configured to communicate with the vehicle controller to receive data on whether a passenger rides in the vehicle, a position of a switch operation of the passenger, and the number of times of the switch operation. The controller of the drone 10 may be interlocked with the vehicle controller to determine the infected area and set the flight path of the drone 10 on the basis of the determined infected area. In addition, since the controller of the drone 10 is configured to select a part for performing intensive sterilization, sterilization of the infected area may be performed through an ultraviolet (UV) light-emitting diode (LED) 14 and the disinfectant applying part 15. In addition, the drone 10 is configured to determine air quality through the vehicle controller or the controller of the drone 10. When the air quality is less than and equal to a second setting value, the drone 10 is controlled to improve the air quality through a purification unit 17 which is located in an area adjacent to the propeller 12 of the drone 10. The purification unit 17 is configured to be located at a lower end of the propeller 12 and to perform purification of air introduced into a filter according to a driving of the propeller 12. The controller is configured to perform a turning flight or hovering of the drone 10 in the vehicle interior. In one form of the present disclosure, the air quality does not merely mean an amount of dust in the air but means a measured value including an amount of germs distributed in the vehicle interior.

In addition, the controller may be configured to perform irradiation of the UV LED 14 to correspond to the infected area and configured to control a direction of the disinfectant applying part 15. In addition, the controller may store a space map of the vehicle interior using the terrain sensors 13, receive measured space data of the vehicle interior in real time to perform determination of an infected area, and set a flight path of the drone 10.

In performing the intensive sterilization of the vehicle interior by the drone 10, the determination of the infected area is preceded so that an area in which a movement of the user is present is determined as the infected area through the terrain sensors 13 located in the drone 10. In addition, the vehicle controller is configured to receive a switch input or an operation input of the vehicle and determine the infected area by compensating for the movement of the user, which is measured by the controller.

In one form, the controller is controlled to set an area, in which the movement of the user is measured to be greater than or equal to a stored reference movement, as the infected area.

In another form of the present disclosure, an area in which the movement of the user is present may be determined as the infected area through the terrain sensors 13 of the drone 10, or an area in which an operation (switch) input is present may be determined as the infected area through the controller.

When contamination of the infected area is greater than or equal to a first reference value, the flight path of the drone 10 may be set to perform UV sterilization. Alternatively, the flight path of the drone 10 may be set through the controller so as to perform disinfectant application of the drone 10. Another form of the present disclosure, the drone 10 may be configured to operate the UV LED 14 and, simultaneously, perform the disinfectant application.

In one form of the present disclosure, when the infected area is greater than or equal to a reference area, the controller may be configured to perform intensive sterilization using the disinfectant applying part 15 and, when the infected area is less than the reference area, the controller may be configured to perform the intensive sterilization using the UV LED 14.

When a passenger is present, the controller determines a position of the passenger using the terrain sensors 13 or a sensor part of the vehicle. When the intensive sterilization is performed, the controller controls the drone 10 to set a flight path in an area not degrading stability of the passenger. In one form, the controller may perform control of compensating for an irradiation height of the UV LED 14 in the area in which the passenger is present and limiting a range of the disinfectant application.

As shown in FIG. 1, the UV LED 14 may be located at the lower end of the drone 10 as one or more UV LEDs 14, and each of the one or more UV LEDs 14 includes a rotating part configured to be rotated in a left-right direction and an LED configured to be lighted at a lower end of the rotating part. In addition, the LED may be configured to be rotated in a vertical direction around both side ends of the rotating part to allow UV to be irradiated in a height direction. Therefore, the UV LED 14 of the present disclosure may be configured to have an irradiation direction of 360 degrees.

FIG. 2 illustrates the disinfectant applying part 15 located at the lower end of the drone body 11.

The vessel located in the drone body 11 is configured to store disinfectant, and the applying part 15 configured to be rotated at 360 degrees based on a lower surface of the vessel is included at a lower end of the vessel. In one form of the present disclosure, two applying parts 15 branching off from the vessel may be included, and each of the two applying parts 15 is configured to be rotated based on the vessel to allow the disinfectant to be sprayed downward.

The two applying parts 15 are configured to have a predetermined angle in a direction opposite to each other based on the height direction of the drone body 11. In addition, the two applying parts 15 are configured to be rotated through the controller and allow the disinfectant located in the vessel to be sprayed to lower end portions of both side surfaces based on the drone 10.

FIG. 3 illustrates a side cross-sectional view of a purification unit 17 for performing a function of purifying air according to one form of the present disclosure.

As shown in the drawing, the purification unit 17 is configured to be located at the lower end of the propeller 12 and is configured to allow air, in which a downflow occurs according to the driving of the propeller 12, to be introduced into the purification unit 17. In addition, the purification unit 17 may include a high-efficiency particulate air (HEPA) filter to perform removal of germs and dusts contained in the air being introduced. In one form, the purification unit 17 may be configured to be driven always or to allow an opening facing the HEPA filter to be selectively opened and closed.

In summary, the controller of the drone 10 of the present disclosure is interlocked with the vehicle controller to determine the infected area in consideration whether the passenger is present in the vehicle interior and provides the flight path of the drone 10 for performing the intensive sterilization using the UV LED 14, the disinfectant, and the purification unit 17 and control of the drone 10 for performing sterilization.

Figure 4:
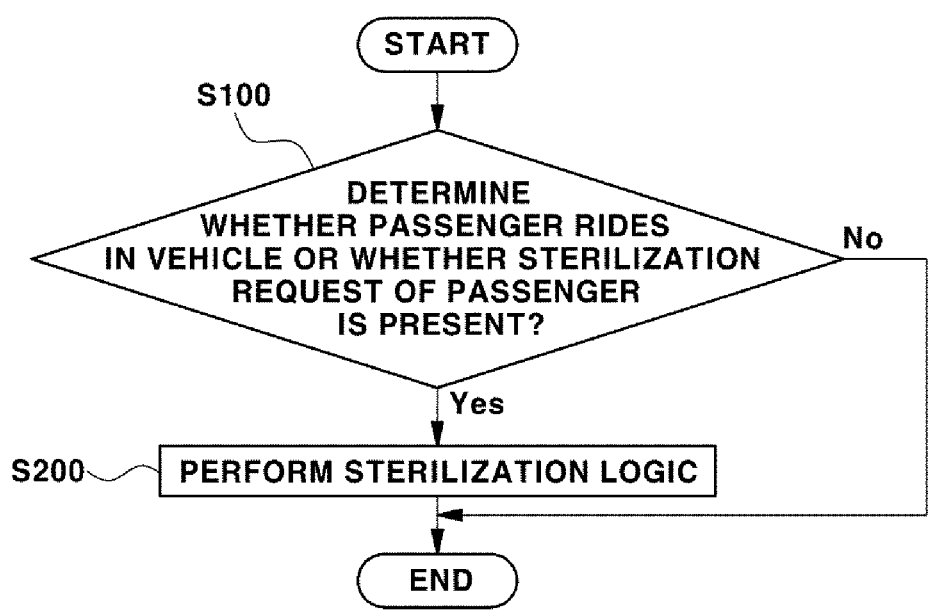
FIG. 4 is a flowchart illustrating a method of sterilizing a vehicle interior using a drone according to one form of the present disclosure.

FIG. 4 illustrates a flowchart of a method of sterilizing a vehicle interior using the drone 10 according to one form of the present disclosure.

The present disclosure is configured to determine whether the passenger rides in the vehicle through the vehicle controller. The determination of whether the passenger rides in the vehicle may be performed through a load sensor located in a seat and the terrain sensors 13 located in the drone 10. In one form, when a condition in which a door of the vehicle is opened is satisfied, the sensors may measure whether the passenger rides in the vehicle (S100).

When the passenger gets out of the vehicle or a sterilization request is input by the user, the controller of the drone 10 is configured to perform the sterilization logic (S200). In another form, the sterilization request of the user may be applied through an input of a switch located in the vehicle or an input switch located in the drone body 11. In addition, the drones 10 is configured to allow a sterilization request signal to be applied to the vehicle through a smart device.

The controller may be configured to be interlocked with the vehicle controller to determine whether the passenger is present by measuring whether the door of the vehicle is opened and a load is applied to a seat of the vehicle after the door is opened and determine whether the passenger is present by performing learning of a space of the vehicle interior and measuring a change in space of the vehicle interior in real time through the terrain sensors 13 of the drone 10.

As described above, when the passenger is not present in the vehicle interior or according to the request of the user, the present disclosure is configured to perform sterilization of the infected area by performing a flight of the drone 10.

In addition, since the drone 10 is capable of setting the flight path according to the presence or absence of the passenger, the drone 10 is controlled to perform a flight to the infected area on the basis of safety of the passenger. For example, the drone 10 determines the presence of the passenger on the basis of data received from the terrain sensors 13 or the vehicle controller, and the drone 10 is controlled to limit disinfectant application in an area adjacent to the passenger. In addition, an irradiation angle of the UV LED 14 is controlled to be lower than a field of view of the passenger to perform prevention of dazzle of the passenger. As such, when the passenger is present, the controller is configured to compensate for the irradiation angle of the UV LED 14 and a spraying area of the disinfectant.

In addition, the controller is configured to receive a change value of the vehicle interior, which is measured in real time, and reset the flight path of the drone 10 in response to the change value, thereby preventing a collision of the drone 10 in a narrow space of the vehicle interior. In addition, the controller is configured to receive data on a driving environment and a driving path of the vehicle from the vehicle controller and control a horizontal movement and a height movement of the drone 10 according to the driving of the vehicle, thereby directing the drone 10 to be located at a position converged by the controller based on the vehicle interior.

Figure 5:
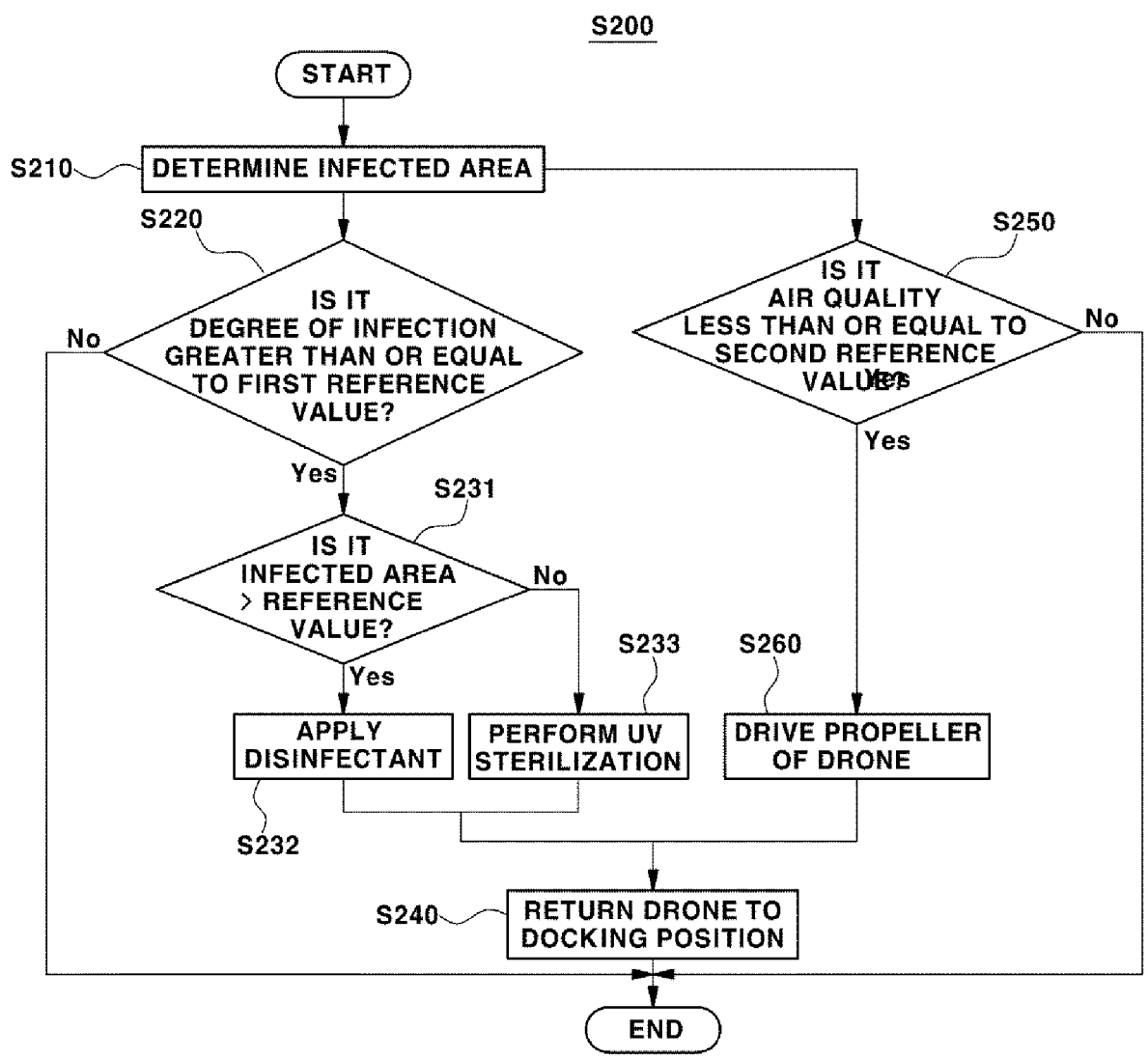
FIG. 5 is a flowchart illustrating a logic for performing intensive sterilization according to one form of the present disclosure.

FIG. 5 is a flowchart illustrating a method of controlling the drone 10 for performing intensive sterilization according to one form of the present disclosure.

The controller is configured to determine the infected area in the vehicle interior (S210). The infected area and a degree of infection are determined through the controller of the drone 10 and the vehicle controller. The controller of the drone 10 measures a movement in the vehicle interior using the terrain sensors 13 and, when the movement is greater than or equal to a reference value, the controller determines an area as the infected area. In addition, the controller of the drone 10 determines a switch input value which is input to the vehicle controller, the number of times of steering, the number of times of a gear shift times, and the like to determine the infected area of the vehicle interior. Thus, when a degree of the movements or the number of input times is greater than or equal to the reference value, a corresponding position is determined an area as the infected area.

When the corresponding position is determined as the infected area through the controller, the degree of infection is determined. When a pollution degree of the infected area is greater than or equal to the first reference value, the controller is configured to perform the intensive sterilization (S220). In addition, when air quality of the vehicle interior is less than or equal to a second reference value (S250), the controller is configured to perform air purification of the purification unit 17 by driving the propeller 12 (S260). The air quality of the present disclosure does not merely mean an amount of dust in air but means a case in which an amount of germs measured in the air is greater than or equal to a reference value.

In one form, the controller of the present disclosure may determine a size of the infected area. When a degree of infection in the infected area is greater than a degree of infection in a reference area which is set to be greater than or equal to the first reference value (S231), the controller controls the drone 10 to apply the disinfectant (S232). When the degree of infection in the infected area is less than the degree of infection in the reference area which is set to be greater than or equal to the first reference value (S231), the controller performs the sterilization logic through the UV LED 14 (S233).

Since the degree of infection is determined by the pollution degree in the infected area, the controller determines that contamination of the infected area is severe as the number of times for the user in contact with a predetermined position in the vehicle interior is increased and a contact time is longer.

As described above, the controller is configured to perform determination of the size of the infected area and measure the pollution degree of the infected area, thereby performing the UV sterilization or the disinfectant application. In a state in which the air quality is degraded, the controller controls to perform the operation of the propeller 12 of the drone 10 so as to drive the purification unit 17. In addition, when the degree of infection is greater than or equal to the first reference value, the infected area is larger than a set area of the controller, and the air quality is less than or equal to the second reference value, the controller may simultaneously perform the UV sterilization and the disinfectant application using the drone 10 and the intensive sterilization using the purification unit 17.

As described above, in a state in which the intensive sterilization is completed, the drone 10 is configured to return to a docking position in the vehicle interior or a docking position located outside the vehicle (S240).

The present disclosure can obtain the following effects according to a combination of the above-described forms and a configuration, which will be described below, and a use relationship.

In accordance with the present disclosure, a sterilization method of automatically performing sterilization of an infected area using a drone can be provided so that there is an effect of improving a use environment of a user.

In addition, different sterilization manners can be provided according to a degree of infection and the size of the infected area so that there is an effect of increasing user convenience.

The foregoing detailed description illustrates the present disclosure. Further, the foregoing is intended to illustrate and describe the exemplary forms of the present disclosure, and the present disclosure may be used in various other combinations, modifications, and environments. That is, it is possible to practice alternations or modifications without departing from the scope of the present disclosure disclosed in this specification, equivalents, and/or within the technical or knowledge scope in the art to which the present disclosure pertains. The described forms are intended to illustrate the best mode for carrying out the technical spirit of the present disclosure and various modification can made in the specific applications and uses of the present disclosure. Therefore, the detailed description is not intended to limit the present disclosure as in the disclosed forms. Further, it should be construed that the appended claims are intended to include another form.

What is claimed is:

1. A method of sterilizing a vehicle interior using a drone, the method comprising:
   receiving information on whether a passenger is boarding or the passenger has initiated a sterilization request; and
   when the passenger is not present in a vehicle interior or the sterilization request is received from the passenger, performing, with a drone, a set of instructions to implement a sterilization logic, wherein the sterilization logic includes:
   determining an infected area using a sensor part; and
   allowing the drone to fly and performing an intensive sterilization in the infected area,
   wherein determining the infected area using the sensor part includes:
   determining a movement of a user by a terrain sensor located in the drone; and
   determining an area in which the movement of the user is greater than or equal to a reference movement stored in a controller as the infected area,
   wherein, when a pollution degree of the infected area is greater than or equal to a first reference value, performing the intensive sterilization includes performing ultraviolet (UV) sterilization or disinfectant application, and
   wherein, when an infected zone of the infected area is greater than a reference area which is set by a controller, performing the intensive sterilization includes applying disinfectant.

2. The method of claim 1, wherein, when the infected zone of the infected area is smaller than the reference area, performing the UV sterilization or the disinfectant application further includes performing the UV sterilization.

3. The method of claim 1, wherein, when air quality of the infected area is less than or equal to a second reference value, performing the intensive sterilization further includes: driving a propeller of the drone and performing air purification by a purification unit.

4. The method of claim 1, wherein determining the movement of the user includes:
   determining, by a vehicle controller, whether a switch input of the user is received; and
   when the determined area where the movement of the user is equal to or greater than the reference movement coincides with an area from which the switch input of the user is received, determining the determined area as the infected area.

5. The method of claim 1, wherein allowing the drone to fly and performing the intensive sterilization in the infected area include:
   learning and storing a terrain of the vehicle interior using the terrain sensor located in the drone; and
   receiving real-time terrain information according to a flight of the drone and setting a flight path.

6. The method of claim 5, wherein allowing the drone to fly and performing the intensive sterilization in the infected area include: when the passenger is present, compensating for a range of ultraviolet (UV) sterilization and disinfectant application.

7. The method of claim 1, further comprising:
   after allowing the drone to fly and performing the intensive sterilization in the infected area are completed, directing the drone to be docked in a vehicle in a standby state.

* * * * *